United States Patent [19]

Minton et al.

[11] Patent Number: 4,693,984
[45] Date of Patent: Sep. 15, 1987

[54] METHOD AND APPARATUS FOR SEQUENTIAL FRACTIONATION

[75] Inventors: Allen P. Minton, Bethesda, Md.; Arun K. Attri, New Delhi, India; James V. Sullivan, Bowie, Md.

[73] Assignee: The United States of America as represented by the Secretary of the Department of Health and Human Services, Washington, D.C.

[21] Appl. No.: 925,452

[22] Filed: Oct. 31, 1986

Related U.S. Application Data

[63] Continuation-in-part of Ser. No. 724,033, Apr. 16, 1985, abandoned.

[51] Int. Cl.⁴ .............................................. G01N 1/18
[52] U.S. Cl. ................................. 436/180; 73/863.21; 222/319; 222/386; 422/100
[58] Field of Search ............................ 73/61.4, 863.21; 141/253, 275, 276; 210/359, 927, 781; 222/319, 386, 390; 422/100, 101, 73; 436/70, 174, 177, 180

[56] References Cited

U.S. PATENT DOCUMENTS

| | | | |
|---|---|---|---|
| 1,714,482 | 5/1929 | Schmuziger | 222/386 X |
| 2,376,231 | 5/1945 | Cohn . | |
| 3,151,639 | 10/1964 | Allington . | |
| 3,418,080 | 12/1968 | Rochte et al. . | |
| 3,501,273 | 3/1970 | Agner . | |
| 3,590,889 | 7/1971 | Vannus . | |
| 3,917,318 | 11/1975 | Legris | 285/150 X |
| 3,954,614 | 5/1976 | Wright | 210/927 X |
| 4,197,735 | 4/1980 | Munzer et al. | 73/61.4 |
| 4,305,303 | 12/1981 | Thies | 73/863.21 |
| 4,346,608 | 8/1982 | Olenick et al. | 422/101 X |

OTHER PUBLICATIONS

Attri et al; Technique and Apparatus for Automated Fractionation of the Contents of Small Centrifuge Tubes Anal. Biochem. 152, 319–328 1986.

Coombs; Density Gradient Fractionation by Piston Displacement; Anal. Biochem. vol. 68, pp. 95–101 (1975).

Primary Examiner—Barry S. Richman
Assistant Examiner—Michael S. Gzybowski
Attorney, Agent, or Firm—Browdy and Neimark

[57] ABSTRACT

An apparatus for sequentially fractionating a centrifuge tube includes a capillary tube and a means for applying positive pressure. The capillary tube has an O-ring at the lower end thereof. As the capillary tube is placed within the centrifuge tube, the O-ring forms a seal within the tube. Movement of the capillary tube within the centrifuge tube places the liquid in the centrifuge tube under pressure, thus forcing the liquid to flow up through the capillary tube and into a chamber. A chase fluid is then pumped horizontally through the chamber to force the liquid therein through an exit port and into a fraction collector. The apparatus and method of the present invention may be entirely automated and controlled by a single microprocessor.

13 Claims, 4 Drawing Figures

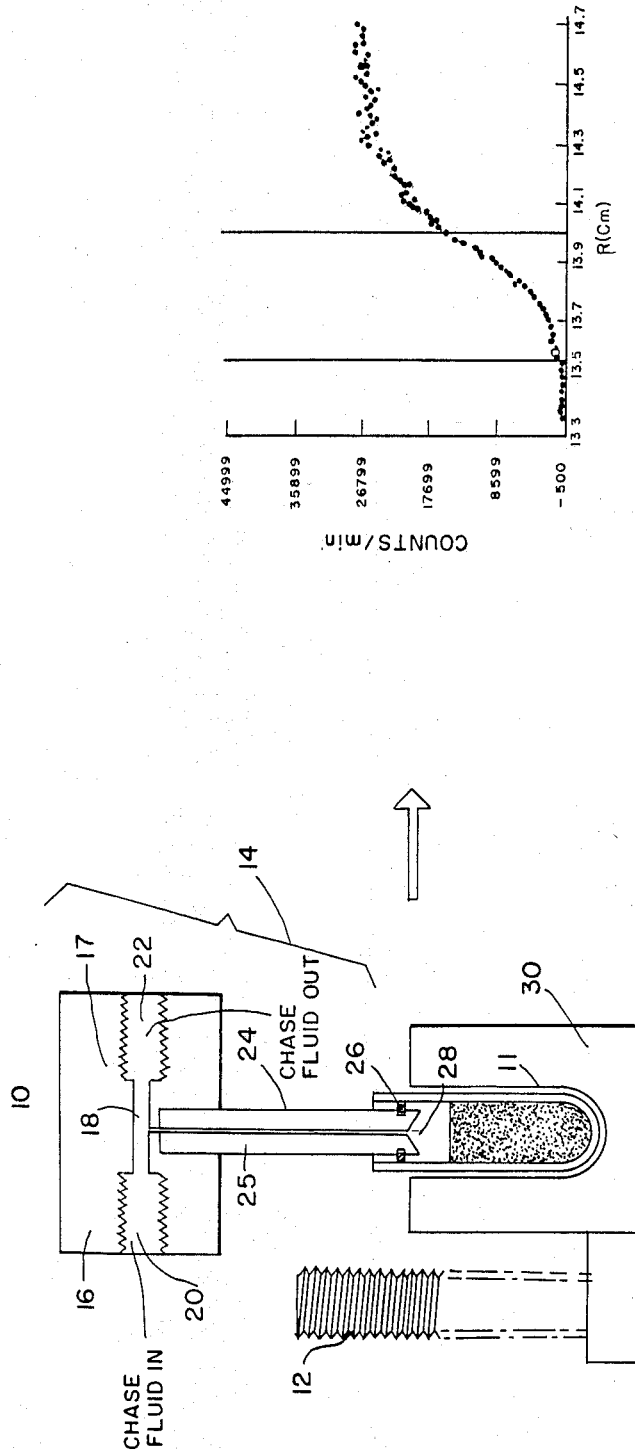
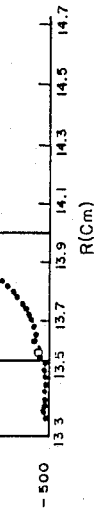
FIG. 3
FIG. 4
FIG. 1

METHOD AND APPARATUS FOR SEQUENTIAL FRACTIONATION

This is a continuation-in-part of present copending application Ser. No. 724,033, filed Apr. 6, 1985, now abandoned.

FIELD OF THE INVENTION

This invention relates generally to fractionators and more particularly to sequential fractionators.

BACKGROUND OF THE INVENTION

Centrifugation has often been employed as a separation technique. In many fields, such as genetic engineering, materials are separated by centrifugation and sedimentation within a cesium chloride or other density-type gradient. After centrifugation and sedimentation, fractions of the centrifuge tube are removed and analyzed. The density of a substance determines where within the cesium chloride gradient the substance settles. This position within the gradient can be specified in terms of a distance from the center of rotation. The density of the substance can be determined by knowing the gradient and the distance from the center of rotation at which the substance settled. Thus, not only can substances of varying densities be separated by this method, but accurate density determinations may also be made.

From the above discussion, it can be understood that the degree of separation achieved, or the precision within which the density of a substance can be determined, is dependent upon the degree to which fractions (or layers) can be removed from the centrifuge tube for analysis without mixing between the layers.

One apparatus disclosed for sequential fractionation is described by Chervenka et al in U.S. Pat. No. 4,181,700. The device include a microsyringe mounted to a movable frame and a suction means for withdrawing fluid from the centrifuge tube into the syringe. The syringe is lowered a precise distance into a centrifuge tube and this distance is read from a micrometer and recorded. Suction is then applied to the syringe tip to remove a precise volume of liquid from the top of the centrifuge tube. While the above method is tolerable for many applications, serious difficulties arise if high precision is desired.

As stated above, precision is related to the degree of mixing which occurs between layers. When suction is applied through the syringe, flow occurs within the centrifuge tube. Since laminar flow laws apply, it is clear that liquid at the center of the tube flows faster than liquid at the outer edges. Thus, a significant amount of mixing inherently occurs.

Another apparatus (U.S. Pat. No. 3,151,639 to Allington) sequentially removes layers from a centrifuge tube by forcing a dense liquid into the bottom of the centrifuge tube to raise the level of the other liquid in the tube an amount corresponding to the volume of the added dense liquid. The liquid in the centrifuge to is forced out of the tube and into a fraction collector solely by the action of the added dense liquid. Although the application of suction is avoided by this method, large amounts of laminar flow and thus mixing still occur, since each time dense fluid is added, the entire liquid mass within the centrifuge tube must move upwardly.

SUMMARY OF THE INVENTION

A general object of the invention is to overcome deficiencies in the prior art, such as indicated above.

It is an object of the present invention to provide for improved sequential fractionation, such as by providing a method and apparatus for sequentially fractionating a centrifuge tube into precise fractions.

It is another object of the present invention to provide a method and apparatus for sequentially fractionating a centrifuge tube with a minimum amount of mixing between fractions.

It is a further object of the present invention to provide a method and apparatus for sequentially fractionating a centrifuge tube without using a vacuum upon the centrifuge tube.

These and other objects are achieved by the use of a capillary tube and positive pressure. The capillary tube has an O-ring at the lower end thereof. As the capillary tube is placed within the centrifuge tube, the O-ring forms a seal within the tube. Movement of the capillary tube within the centrifuge tube places the liquid in the centrifuge tube under pressure, thus forcing the liquid to flow up through the capillary tube and into a chamber. A chase fluid is then pumped horizontally through the chamber to force the liquid therein through an exit port and into a fraction collector. The apparatus and method of the present invention may be operated by hand or may be entirely automated and controlled by a single microprocessor.

BRIEF DESCRIPTION OF THE DRAWINGS

FIG. 1 schematically shows a preferred embodiment of the present invention.

FIG. 3 graphically illustrates results obtained using the present invention.

FIG. 4 also graphically illustrates results obtained using the present invention.

DESCRIPTION OF PREFERRED EMBODIMENTS

Figure 2:
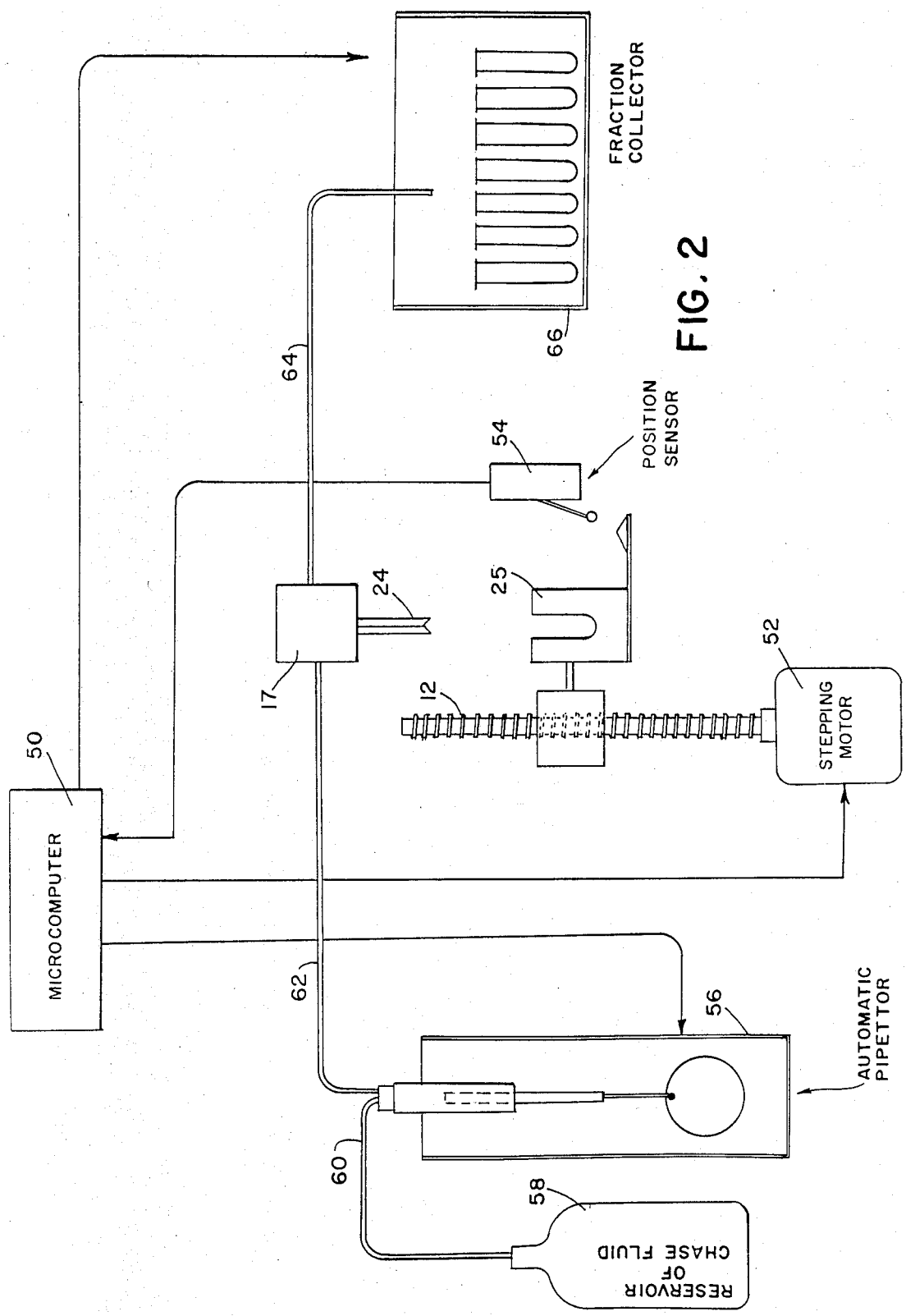
FIG. 2 schematically shows a preferred embodiment for automating the present invention.

Preferably, the centrifuge tube used is precision made. In other words, the inner diameter of the tube should be essentially uniform. The degree of acceptable variance in this regard depends on the precision and accuracy desired. Generally, the precision of the present invention is limited to twice the variance in the centrifuge tube inner diameter consistency.

The capillary tube used preferably has a small inner diameter and a volume of no more than about twice that of the desired sample size so that the area in which flow can occur is as small as possible. The end of the capillary tube which is to be inserted into the centrifuge tube is outwardly flared, preferably at an angle of about 30°60° from the vertical axis. The outward flare or conical configuration help to minimize the removal of liquid from the center portion of the centrifuge tube at a faster rate than from the sides of the centrifuge tube, and thereby serves to minimize undesirable mixing of adjacent horizontal layers of liquid.

Both the capillary tube and the centrifuge tube should be supported so that they stand along the same vertical axis. The capillary tube is vertically lowered, or the upright centrifuge tube raised, so that the capillary tube is inserted, flared end down, into the upright centrifuge tube by a suitable means for precision movement. The means for precision movement need only move the centrifuge tube along the vertical axis relative to the capillary tube. Thus, either the capillary tube, the centrifuge tube or both may actually be moved. A starting point is obtained and a measurement of the vertical distance moved by the capillary tube or centrifuge tube is taken by any well-known suitable means, such as a calibrated micrometer directly connected to the means for lowering the capillary tube.

As the capillary tube is inserted into the centrifuge tube, an O-ring on the capillary tube, positioned just above the flared end, sealingly engages the inside surface of the centrifuge tube and provides positive pressure upon the liquid therein. As the capillary tube is further inserted and its depth within the centrifuge tube increased, this positive pressure forces the surface fraction of liquid into and through the capillary tube and finally into a chamber connected to the non-flared upper end of the capillary tube. In addition to an opening connecting the chamber to the capillary tube, the chamber has an exit port and an entrance port providing for the horizontal movement (transverse to the vertical axis) of fluid from the entrance port to the exit port. The entrance port is connected to a pump for applying horizontal fluid pressure within the chamber. This horizontal fluid pressure forces any liquid within the chamber through the exit port. The exit port is connected to a standard fraction collector.

From the above description, it can be seen that little or no mixing of flow occurs in the centrifugal tube during the removal of fractions. Of course, significant flow and mixing does occur in the capillary tube. Nevertheless, because of the relatively small diameter and small volume of the capillary tube relative to the desired sample size, the effect of this mixing on precision and accuracy are almost negligible. To this end, the ratio of the cross-sectional area of the chamber to the internal cross-sectional area of the capillary tube is preferably at least about 10:1. Obviously, larger ratios of cross-sectional areas may be used, depending on the degree to which the fraction is to be diluted with chase fluid.

In a preferred embodiment 10, as shown in FIG. 1, the means to move the centrifuge tube 11 (preferably a high precision quartz tube) or capillary tube relatively closer to each other along a vertical axis is a precision screw drive 12 coupled by means of a transmission (not shown) to a stepping motor (52 in FIG. 2). Using this apparatus, elevation of the centrifuge tube can be controlled to ±0.0003 cm.

A stationary fluid removal port 14 consists of two sections joined as illustrated in FIG. 1. The upper section of the port is a block 16 (suitably formed of Lucite, Plexiglas or other machinable rigid plastic, preferably transparent) containing a chamber 17 defined by a horizontal capillary 18 of 1 mm diameter between two opposing fittings 20, 22 for the connection of external tubing. The lower section of the port is a vertically mounted stainless steel cylinder 24, desirably of stainless steel, of 3.1 mm OD, housing a capillary 25 of 0.3 mm diameter along the cylindrical axis. An O-ring 26 seated at the bottom end of the cylinder provides a gas- and liquid-tight seal when the cylinder is inserted into the mouth of a miniature quartz centrfuge tube 11. An outwardly flared (preferably about 45°) aperture 28 at the bottom end of the cylinder 24 guides tube contents to the capillary 25. The upper end of the cylinder 24 is fixed into the Lucite block 16 so that the vertical capillary 25 exiting from the upper end of the cylinder 24 enters perpendicularly into the horizontal capillary 18, forming a T-connection.

In order to operate the device, a peristaltic or repeating syringe pump (56 and 58 in FIG. 2), capable of delivering 2-3 ml of liquid in a few seconds on demand, is connected via tubing to fitting 20, and a fraction collector (66 in FIG. 2) is connected via tubing fitting 22. A receptacle 30, for holding the centrifuge tube 11, is moved to the lower limit of its travel, and the quartz centrifuge tube 11 containing the solution to be fractionated placed therewithin.

The centrifuge tube 11 is then elevated by means of the screw drive 12 until the lower end of the fluid removal port 14 enters the mouth of the stainless steel capillary 24, 25. Insertion of the port 14 is facilitated by prior application of a small amount of silicone grease to the O-ring 26. The centrifuge tube 11 is then further elevated slowly until solution at the meniscus enters the stainless steel capillary 24, 25 and a small amount of liquid is subsequently observed to enter the horizontal capillary 18 within the Lucite block 16.

At this stage a starting point is obtained, and the micrometer is set to zero, or preferably control of the apparatus is transferred to a microcomputer (50 in FIG. 2). The user enters the desired increment of radial distance corresponding to an individual fraction and the desired number of fractions.

The following procedure is then performed repetitively without manual intervention until the desired number of fractions have been collected: (1) The centrifuge tube is elevated by the designated distance. (2) That amount of solution driven into the horizontal capillary upon elevation is flushed with 2 to 3 ml of carrier fluid into a collecting vial mounted in the fraction collector. (3) The fraction collector is advanced to the next vial.

One use of the present invention is to measure concentration gradients of radiolabeled solutes subjected to prior application of centrifugal force. The carrier fluid used may be scintillation fluid, and the collecting vessels may be glass vials which, after fractionation, are placed in a scintillation counter for measurement of the amount(s) of one or more radiolabeled species in each fraction. However, quantitation of concentratoin gradients is not limited to radiolabeled solutes: in principle, any chemical or physical assay of the requisite sensitivity may be utilized, as, for example, an assay of enzyme activity to measure the amount of enzyme in each fraction.

FIG. 2 schematically illustrates an automatic fractionator according to the present invention.

Microcomputer 50 signals stepping motor 52 to raise receptacle 30 with centrifuge tube 11 thereon by turning screw drive 12. Receptacle 30 activates position sensor 54, thus send a signal to microcomputer 50 and establishing a reference point. The microcomputer is programmed to raise receptacle 30 in increments sufficient to raise a volume of solution equal to the selected sample volume into capillary 25. After the sample flows into capillary 25, it flows into chamber 17 and microcomputer 50 sends a signal to automatic pipetter 56, which draws fluid from the reservoir of chase fluid through line 60 and pumps the fluid through line 62 into chamber 17, thus chasing the sample into line 64 and finally to the fraction collector 66, which is also controlled by microcomputer 50 and collects fractions in an ordered manner according to fraction number.

By way of example, the microcomputer 50 may be an Epson HX-20, the automatic pipetter may be an Oxford automatic pipetter, and the fraction collector may be a Gilson 201B fraction collector.

EXAMPLES

Having fully described the invention above, the following examples are given solely for illustrative purposes and are not intended to limit the scope of the invention in any manner.

FIGS. 3 and 4 show results obtained from fraction of solutions of $^{131}$I- labeled bovine serum albumin centrifuged under two different sets of conditions.

In FIG. 3 the relative protein concentration in an aliquot, expressed as counts per minute, is plotted as a function of the radial position of the aliquot during centrifugation, measured at the conclusion of a sedimentation velocity experiment. Approximately 150 ul of 0.04 mg/ml protein solution were required to perform this measurement. Resolution of the data is 10 points/nms or radial distance. The vertical line to the left of the plot indicates the position of the solution meniscus (upper boundary), and the vertical line to the right indicates the weight-average position of the trailing boundary of sedimenting protein, as calculated from the data. The sedimentation coefficient calculated from these data is in good agreement with published values.

In FIG. 4 the natural logarithm of the relative protein concentration in an aliquot, expressed as 1n (counts per minute), is plotted as a function of the square of the radial position of the aliquot during centrifugation, measured at the conclusion of a sedimentation equilibrium experiment. Approximately 40 ul of a 0.02 mg/ml protein solution were required to perform this measurement. Sedimentation theory predicts that this plot should be linear for a homogeneous species at sedimentation equilibrium. The molecular weight of the protein, calculated from the slope of this plot, is in good agreement with published values.

It is to be understood that the present invention is not limited to the embodiments disclosed which are illustratively offered and that modifications may be made without departing from the invention. For example, the present invention can be substantially increased in size, always keeping the volume of the small diameter tube (even though larger than capillary size) less than about twice the volume of the desired sample size, to perform various separation functions.

What is claimed is:

1. An apparatus for removing fractions of a predetermined volume from a holding tube containing a liquid, with a concentration gradient of solute therein, comprising:

a capillary tube, for removing a fraction of a predetermined volume from a holding tube containing a liquid with a concentration gradient of solute therein, said concentration gradient including a plurality of said fractions of said predetermined volume;

said capillary tube having a bottom internal end flared outwardly at an angle of between 30 and 60° and having sealing means, for slidably sealing a bottom external end of said capillary tube within the interior of said holding tube, located above the flared end of said capillary tube;

means for mounting said capillary tube along a vertical axis with said outwardly flared internal end facing downward;

means for mounting said holding tube in an upright orientation below said capillary tube and along said vertical axis, and for placing said capillary tube into said holding tube so as to sealingly engage said sealing means with the interior surface of said holding tube;

means defining a chamber connected to an end of said capillary tube opposite to said outwardly flared internal end, said chamber having a cross-sectional area at least about ten times larger than an internal cross-sectional area of said capillary tube, so as to essentially prevent mixing of the gradient in said holding tube when fractions are removed from said holding tube;

means for providing relative incremental movement of said capillary tube and said holding tube to force a layer of liquid from said holding tube into said capillary tube, and eventually into said chamber means; and means for exerting fluid pressure within said chamber in a horizontal direction, wherein said fluid pressure forces any liquid within said chamber horizontally through an exit port in said chamber.

2. The apparatus of claim 1, wherein the ratio of the cross-sectional area of said chamber to the inner cross-sectional area of said capillary tube is about 10:1.

3. the apparatus of claim 1, wherein said holding tube has a substantially uniform inner diameter.

4. The apparatus of claim 3 further comprising a means for determining a reference point along a length of said holding tube.

5. The apparatus of claim 4 further comprising a microcomputer, said microcomputer including:
means for setting a desired number of fractions;
means for setting a desired sample volume
means for activating said means for providing relative incremental movement;
means for recording said reference point;
means for activating said fluid pressure exerting means to force a sample within said chamber through said exit port and into a fraction collector;
means for causing said fraction collector to collect each fraction in an ordered manner according to fraction number.

6. The apparatus of claim 3, wherein the connection between the end of said capillary tube opposite said flared end and said chamber defines a T-connection.

7. The apparatus of claim 6, wherein said chamber comprises a capillary means having two open ends and a middle portion therebetween, said middle portion having a means defining an opening for connecting to said capillary tube, each of said ends having a fitting attached thereto, one of said fittings being connected to said means for exerting fluid pressure.

8. The apparatus of claim 7, wherein the other fitting is connected to a fraction collector.

9. A method of removing fractions from a centrifuge tube having a concentration gradient of solute therein, comprising the steps of:

(a) selecting a fraction volume;

(b) selecting a capillary tube having a volume of no more than about twice the volume of said selected fraction volume said capillary tube having one internal end flared outwardly at an angle of between 30° to 60° and having an O-ring having an outer diameter slightly smaller than the inner diameter of said centrifuge tube, said O-ring being fitted externally about said capillary tube above the flared end thereof;

(c) maintaining said capillary tube, flared side down, along a vertical axis;

(d) positioning a centrifuge tube having liquid therein in an upright orientation below said capillary tube and along said vertical axis;

(e) inserting said capillary tube into said centrifuge tube so as to sealingly engage said O-ring with the interior surface of said centrifuge tube;

(f) increasing the depth at which said flared end of said inserted capillary tube rests within said centrifuge tube so as to cause a first fraction of said selected volume of said liquid to enter said capillary tube;

(g) further increasing the depth at which said flared end of said capillary tube rests within said centrifuge tube so as to cause at least one additional fraction of said selected volume of said liquid and to force at least a portion of said first fraction into a chamber connected to said capillary tube, said chamber having a cross-sectional area sufficiently larger than an internal cross-sectional area of said capillary tube so as to essentially prevent mixing of the gradient in said centrifuge tube;

(h) exerting fluid pressure horizontally across said chamber to force said portion out of said chamber through an exit port in said chamber.

10. The method of claim 9 further comprising the step of collecting said portion of said first fraction forced out of said chamber in a fraction collector.

11. The method of claim 10, wherein steps (f), (g) and (h) are repeated cyclically for all subsequent fractions, said fraction entering said capillary tube during each cycle being regarded as said first fraction with respect to all subsequent fractions entering said capillary tube.

12. The method of claim 9, wherein the ratio of the cross-sectional area of said chamber to the inner cross-sectional area of said capillary tube is at least about 10:1.

13. The method of claim 12, wherein the ratio of the cross-sectional area of said chamber to the inner cross-sectional area of said capillary tube is about 10:1.

* * * * *